(12) United States Patent
Kunita (10) Patent No.: US 8,343,055 B2
(45) Date of Patent: *Jan. 1, 2013

(54) ULTRASOUND DIAGNOSTIC APPARATUS

(75) Inventor: Masanori Kunita, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 537 days.

This patent is subject to a terminal disclaimer.

(21) Appl. No.: 12/480,874

(22) Filed: Jun. 9, 2009

(65) Prior Publication Data

US 2009/0312636 A1      Dec. 17, 2009

(30) Foreign Application Priority Data

Jun. 16, 2008   (JP) ................................ 2008-156770

(51) Int. Cl.
*A61B 8/14* (2006.01)
(52) U.S. Cl. .................. 600/457; 600/453; 600/437
(58) Field of Classification Search .................. None
See application file for complete search history.

(56) References Cited

U.S. PATENT DOCUMENTS

| | | | |
|---|---|---|---|
| 4,167,879 A * | 9/1979 | Pedersen | 73/610 |
| 4,176,351 A | 11/1979 | DeVita et al. | |
| 4,320,765 A * | 3/1982 | Cathignol et al. | 600/455 |
| 4,578,677 A * | 3/1986 | Lewis | 342/201 |
| 4,918,706 A | 4/1990 | Phillips et al. | |
| 5,022,400 A * | 6/1991 | Walters | 600/455 |
| 5,224,482 A * | 7/1993 | Nikoonahad et al. | 600/454 |
| 6,179,781 B1 * | 1/2001 | Phillips | 600/454 |
| 6,918,875 B2 * | 7/2005 | Moriya et al. | 600/443 |
| 6,953,434 B2 * | 10/2005 | Hao et al. | 600/458 |
| 6,960,169 B2 * | 11/2005 | Mao et al. | 600/458 |
| 7,094,204 B2 * | 8/2006 | Banjanin et al. | 600/443 |
| 7,338,450 B2 | 3/2008 | Kristoffersen et al. | |
| 7,698,948 B2 * | 4/2010 | Asafusa et al. | 73/627 |

(Continued)

FOREIGN PATENT DOCUMENTS

CN      86203861 U      11/1987

(Continued)

OTHER PUBLICATIONS

Chinese Office Action dated Mar. 24, 2011, issued in corresponding Chinese Patent Application No. 2009-10147985.X.

(Continued)

*Primary Examiner* — Long V. Le
*Assistant Examiner* — Bradley Impink
(74) *Attorney, Agent, or Firm* — Westerman, Hattori, Daniels & Adrian, LLP (57) ABSTRACT

An FSK modulator 20 applies FSK modulation processing to an RF wave supplied from an RF wave oscillator 22, by means of frequency shift keying (FSK) based on a periodical signal sequence supplied from a pattern generator 24, to thereby generate an FSK continuous wave. The continuous wave output from the FSK modulator 20 is delayed in delay circuits 26I and 26Q and is then supplied, as a reference signal, to each of mixers of a receiving mixer 30. Each of the delay circuits 26I and 26Q delays the continuous wave by a delay amount in accordance with a depth of a target position and outputs a delayed reference signal. Thus, demodulation processing is performed with a correlation between a reception signal from the target position and the reference signal being enhanced, and Doppler information from the target position is selectively extracted by a Doppler information analyzing unit 44.

16 Claims, 11 Drawing Sheets

U.S. PATENT DOCUMENTS

| | | | |
|---|---|---|---|
| 7,887,487 B2* | 2/2011 | Hao et al. | 600/455 |
| 2007/0282203 A1* | 12/2007 | Baba et al. | 600/453 |
| 2008/0269612 A1 | 10/2008 | Kunita | |
| 2009/0312636 A1 | 12/2009 | Kunita | |

FOREIGN PATENT DOCUMENTS

| | | |
|---|---|---|
| EP | 1 695 665 A2 | 8/2006 |
| EP | 1769747 A1 | 4/2007 |
| EP | 1986020 A2 | 10/2008 |
| JP | 2005-253949 A | 9/2005 |
| JP | 2006-14916 A | 1/2006 |
| JP | 2006-288974 A | 10/2006 |
| JP | 2007330541 A | 12/2007 |
| WO | 2006/043603 A1 | 4/2006 |

OTHER PUBLICATIONS

Chinese Office Action dated Mar. 23, 2011, issued in related Chinese Patent Application No. 2009-10143784.2.

European Search Report dated Jan. 28, 2011, issued in related European Patent Application No. 08007852.0.

Wilhjelm J E et al., "Coherent FM Doppler System", 1989 Ultrasonics Symposium Proceedings, Oct. 3, 1989, pp. 903-906.

European Search Report dated Aug. 14, 2009, issued in related European Patent Application No. 09006912.1.

Chinese Office Action dated Feb. 5, 2010, issued in related Chinese Patent Application No. 200810091287.8.

Masanori Kunita; "Range Measurement in Ultrasound FMCW System," Electronics and Communications in Japan, Part 3; vol. 90; No. 1; 2007; pp. 9-19.

USPTO Office Action dated Jan. 28, 2011, issued in U.S. Appl. No. 12/107,461.

European Search Report dated Oct. 5, 2009, issued in corresponding European Patent Application No. 09007364.4.

Office Action dated Nov. 14, 2011, issued in related U.S. Appl. No. 12/477,266.

Notice of Allowance and Fees Due dated Oct. 11, 2011, issued in related U.S. Appl. No. 12/107,461.

USPTO Office Action dated Jun. 22, 2011, issued in U.S. Appl. No. 12/107,461.

Michael Ellis, "Using Mixers in Radio Communications", Mar. 21, 2004, retrieved from the Internet: URL:http://web.archive.org/web/20040321152312/http://michelgellis.tripod.com/mixerscom.html, (9 pages), cited in European Office Action dated Jun. 13, 2012.

European Office Action dated Jun. 13, 2012, issued in corresponding European application No. 09006912.1.

Notice of Allowance and Fees due dated Apr. 24, 2012, issued in copending related U.S. Appl. No. 12/477,266.

Notice of Allowance and Fees Due dated Aug. 6, 2012, issued in related U.S. Appl. No. 12/477,266.

\* cited by examiner

ULTRASOUND DIAGNOSTIC APPARATUS

BACKGROUND

1. Technical Field

The present invention relates to an ultrasound diagnostic apparatus, and more particularly to an ultrasound diagnostic apparatus in which a modulated continuous wave is utilized.

2. Related Art

Continuous wave Doppler is a known ultrasound diagnostic apparatus technology in which a continuous wave is employed. In continuous wave Doppler technology, a transmission wave formed as a sinusoidal wave of several MHz is continuously radiated into a living organism, and a reflection wave from within the living organism is then continuously received. The reflection wave includes Doppler shift information generated by a moving element (e.g. blood flow) within the living organism. Accordingly, by extracting the Doppler shift information and applying frequency analysis thereto, a Doppler waveform which reflects information of velocity of the moving element, for example, can be formed.

Continuous wave Doppler technology in which a continuous wave is utilized is generally superior to Pulse Doppler, in which a pulse wave is utilized, for rapid acquisition of velocity measurements. Under such circumstances, the inventors of the present application have conducted research concerning continuous wave Doppler technology. In one of their achievements, the present inventors proposed the technology concerning Frequency Modulated Continuous Wave Doppler (FMCW Doppler) disclosed in JP 2005-253949 A.

As such, typical continuous wave Doppler devices (i.e., devices in which the FMCW Doppler is not utilized) were unable to perform position measurement. In this regard, the present inventors proposed, in JP 2006-14916 A, a technology which enabled measurement of a position of a tissue within a living organism, in addition to measurement of the velocity of a tissue within the living organism, by using FMCW Doppler.

The FMCW Doppler technology described in the above-noted publications is a revolutionary technology providing a potential for new forms of ultrasound diagnosis. The present inventors have continued to research and improve this landmark technology.

SUMMARY

The present invention was made in view of the above circumstances, and advantageously provides an improved technology for extracting in-vivo information from a target position by using a continuous wave.

In order to achieve the above advantages, in accordance with an aspect of the invention, there is provided an ultrasound diagnostic apparatus including a transmission signal processing unit that outputs a transmission signal which is a continuous wave having been digitally modulated based on a periodical signal sequence; a transmitting/receiving unit that transmits a transmission wave corresponding to the transmission signal to a living organism and receives a reception wave associated with the transmission wave from the living organism, to thereby obtain a reception signal; a reception signal processing unit that applies demodulation processing to the reception signal by using a reference signal formed based on the transmission signal, to thereby obtain a demodulated signal; and an in-vivo information extraction unit that extracts in-vivo information from the demodulated signal, wherein in-vivo information from a target position within the living organism is selectively extracted.

In the above aspect, by adjusting a correlation between a periodical signal sequence of a reception signal obtained from a target position within a living organism and a periodical signal sequence of a reference signal, for example, a reception signal from the target position can be extracted as a signal component having a relatively high degree of correlation with the reference signal. In addition, by extracting Doppler information from the reception signal by means of a band-pass filter or a low pass filter, for example, selective extraction of the in-vivo information from the target position can be achieved. Here, in the above aspect, frequency shift keying, phase-shift keying, amplification shift keying, or the like can be utilized as digital modulation processing. Further, it is desirable that the waveform of the reference signal and the waveform of the transmission signal are completely identical. However, the reference signal and the transmission signal may be in a correspondence relationship, in which their waveforms can be considered to be substantially identical.

According to the present invention, extraction of Doppler information from a target position can be achieved by using continuous waves which have been subjected to digital modulation.

BRIEF DESCRIPTION OF THE DRAWINGS

A preferred embodiment of the present invention will be described in detail by reference to the drawings, wherein.

DETAILED DESCRIPTION

A preferred embodiment of the present invention will be described in detail with reference to the accompanying drawings.

Figure 1:
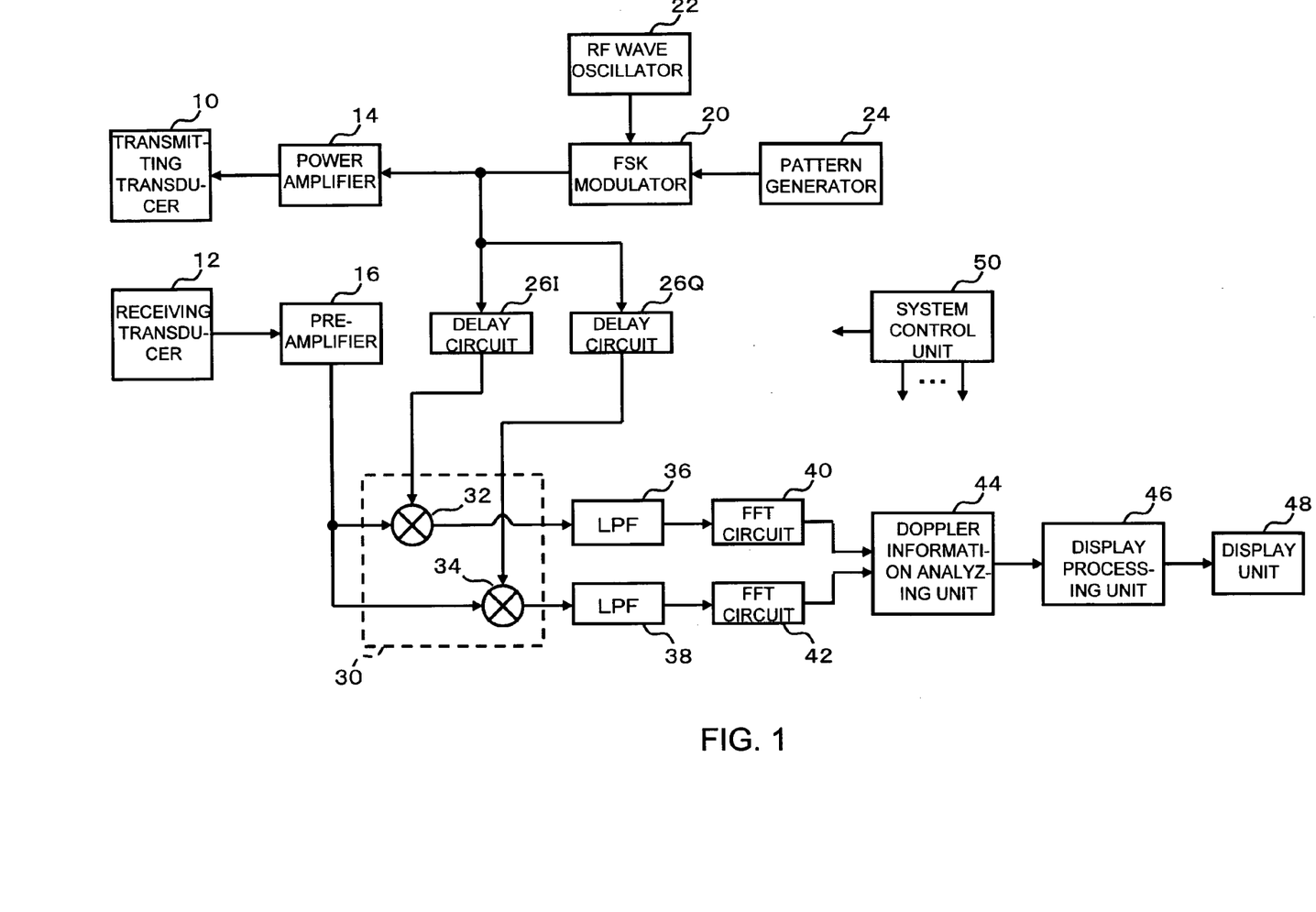
FIG. 1 is a functional block diagram illustrating the overall structure of an ultrasound diagnostic apparatus according to the present invention.

FIG. 1 is a functional block diagram illustrating the overall structure of an ultrasound diagnostic apparatus according to a preferred embodiment of the present invention. A transmitting transducer 10 continuously transmits a transmission wave into a living organism, and a receiving transducer 12 continuously receives a reflection wave from within the living organism. Thus, transmission and reception is performed by different transducers, and transmission/reception by means of a so-called continuous wave Doppler method technology is thus executed. The continuous waves utilized in the present embodiment are digitally modulated continuous waves which are formed by an FSK modulator 20.

The FSK modulator 20, by means of frequency shift keying (FSK) based on a periodical signal sequence supplied from a pattern generator 24, applies modulation processing to an RF wave supplied from an RF wave oscillator 22, to thereby generate an FSK continuous wave. The waveform of the continuous wave which is formed by frequency shift keying (FSK) will be described below. The FSK modulator 20 outputs to a power amplifier 14 a continuous wave which has been digitally (FSK) modulated.

The power amplifier 14 power-amplifies the FSK modulated continuous wave and then supplies the power-amplified FSK modulated continuous wave to the transmitting transducer 10. The transmitting transducer 10 transmits a transmission wave corresponding to the FSK modulated continuous wave. Then, a reflection wave from within the living organism is continuously received by the receiving transducer 12.

A preamplifier 16 applies reception processing such as low-noise amplification to a reception wave signal supplied from the receiving transducer 12 to generate a receiving RF signal, which is output to a receiving mixer 30. The receiving mixer 30, which is a circuit for applying orthogonal detection to the receiving RF signal to generate a complex baseband signal, is composed of two mixers 32 and 34. Each of the mixers is a circuit which mixes the receiving RF signal with a predetermined reference signal.

The reference signal supplied to each mixer of the receiving mixer 30 is generated based on the digitally modulated (FSK modulated) continuous wave (i.e., the transmission signal). Specifically, the continuous wave output from the FSK modulator 20 is delayed in delay circuits 26I and 26Q, respectively. The continuous wave which is delayed by the delay circuit 26I is supplied to the mixer 32, and the continuous wave which is delayed by the delay circuit 26Q is supplied to the mixer 34.

Each of the delay circuits 26I and 26Q delays the continuous wave by a delay amount in accordance with the depth of a target position, and thus outputs a delayed reference signal. Each of the delay circuits 26I and 26Q can be formed of an n-stage shift register, for example. In this case, a tap for a delay amount corresponding to the depth of the target position is selected from n-stage taps of the shift register, and a reference signal corresponding to the depth of the target position (i.e. a delayed continuous wave) is output.

Here, the delay circuits 26I and 26Q perform delay processing by shifting the phases of the respective continuous waves by n/2 with respect to each other. Consequently, the mixer 32 outputs an in-phase signal component (I signal component) and the mixer 34 outputs a quadrature signal component (Q signal component). Then, high frequency components of the in-phase signal component and the quadrature signal component are removed by LPFs (low pass filters) 36 and 38, respectively, which are provided downstream of the receiving mixer 30, so that a demodulated signal having only a necessary bandwidth after detection can be extracted.

As will be described in detail in the following explanation of the technological principle of the present invention, a receiving mixer output signal (i.e. a demodulated signal), which is a result of mixing the receiving RF signal with the reference signal performed in each mixer, contains a large amount of reception signal components from the target position. The LPFs 36 and 38 extract a direct-current(low-frequency) signal component contained in the reception signal components from the target position (if a moving element is present at the target position, a Doppler signal component is contained).

FFT circuits (fast Fourier transform circuits) 40 and 42 execute an FFT operation with respect to each of the demodulated signals (the in-phase signal component and the quadrature signal component). Consequently, the demodulated signal is transformed into a frequency spectrum in each of the FFT circuits 40 and 42. Here, the frequency spectrums output from the FFT circuits 40 and 42 are supplied in the form of frequency spectrum data with the frequency resolution δf, depending on the circuit setting condition or the like.

A Doppler information analyzing unit 44 extracts Doppler information, including a polarity thereof, from the demodulated signals which are transformed into the frequency spectrums. At this time, as the delay relationship between the reference signal and the reception signal has already been adjusted in accordance with the depth of a target position within the living organism by the delay circuits 26I and 26Q, Doppler information from the target position can be selectively extracted. The relevance between the delay adjustment and the extraction of Doppler information from the target position will be described in detail with reference to explanation of the principle of the present invention. The Doppler information analyzing unit 44 extracts the Doppler information for each depth (each position) within the living organism, to thereby compute the velocity of a tissue within the living organism for each depth along the ultrasound beam (sound ray), and outputs the results in real time. Here, the velocity of a tissue at each position within the living organism may be computed in a two- or three-dimensional manner by scanning the ultrasound beam.

A display processing unit 46, based on the velocity of the tissue within the living organism for each depth (position), creates a Doppler waveform or a graph including information concerning the depth velocity, for example, and causes a display unit 48 to display the Doppler waveform and the graphs thus created in real time. Here, each of the units in the ultrasound diagnostic apparatus as shown in FIG. 1 is controlled by a system control unit 50. Specifically, the system control unit 50 performs transmission control, reception control, display control, and so on.

As described above in general terms, according to the present embodiment, an ultrasound wave corresponding to a continuous wave which has been subjected to FSK modulation is transmitted and received to obtain a reception signal, and the delay relationship between the reference signal and the reception signal is adjusted in accordance with the depth of a target position within the living organism, and then demodulation processing is performed with the degree of correlation between the reception signal from the target position and the reference signal being thus increased, so that in-vivo information can be selectively extracted from the target position. Here, the principle for selectively extracting the Doppler information from a target position will be described in detail.

Figure 2:
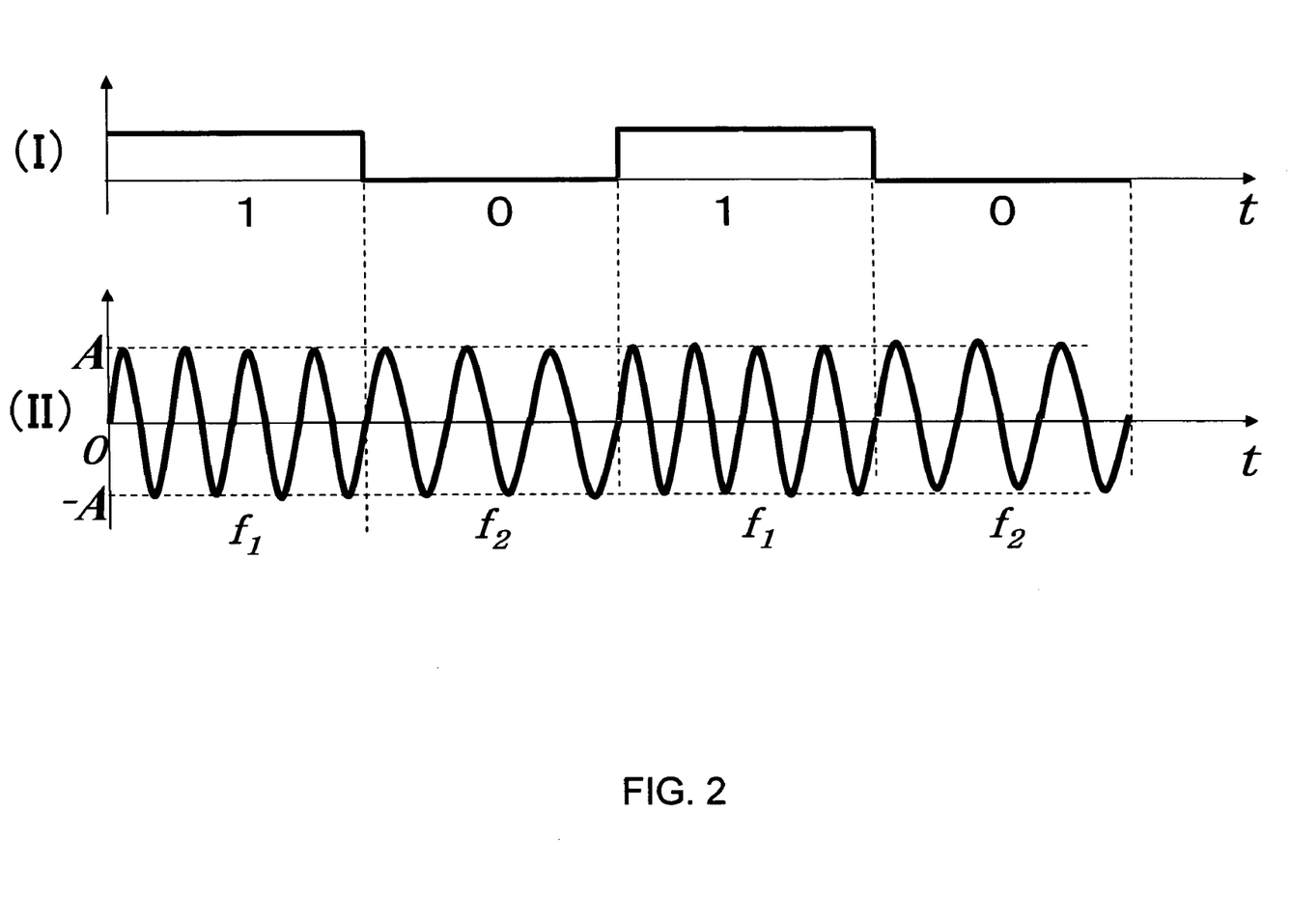
FIG. 2 is a view for explaining a transmission signal which is a continuous wave formed by FSK.

FIG. 2 explains a transmission signal which is a continuous wave formed by means of frequency shift keying (FSK). FIG. 2(I) illustrates an example of a periodical signal sequence output from the pattern generator (designated by reference-numeral 24 in FIG. 1). The pattern generator generates a binary code whose value varies at random (a pseudo random signal), as illustrated in FIG. 2(I), for example. As a code sequence of a pseudo random signal which is a periodical signal sequence, a code sequence which is put into practical use by means of pulse compression or the like, such as a PN (Pseudo Noise) sequence, M sequence, or Gorey sequence, can be used.

FIG. 2(II) illustrates a modulated continuous wave (i.e. a transmission signal) which is formed in the FSK modulator (designated by reference numeral 20 in FIG. 1). The FSK modulator applies FSK modulation processing to the RF wave (carrier wave) by means of frequency shift keying based on the binary code illustrated in FIG. 2(I), to thereby generate a transmission signal which is a continuous wave. The FSK modulator generates a transmission signal of FIG. 2(II) by setting the frequency $f_1$ during a bit period in which the binary code is "1" and setting the frequency $f_2$ during a bit period in which the binary code is "0," for example.

As such, an ultrasound wave which is a continuous wave corresponding to the transmission signal shown in FIG. 2(II), for example, is output from the transmitting transducer (designated by reference numeral 10 in FIG. 1), and a reception signal from the living organism can be obtained via the receiving transducer (designated by reference numeral 12 in FIG. 1).

Figure 3:
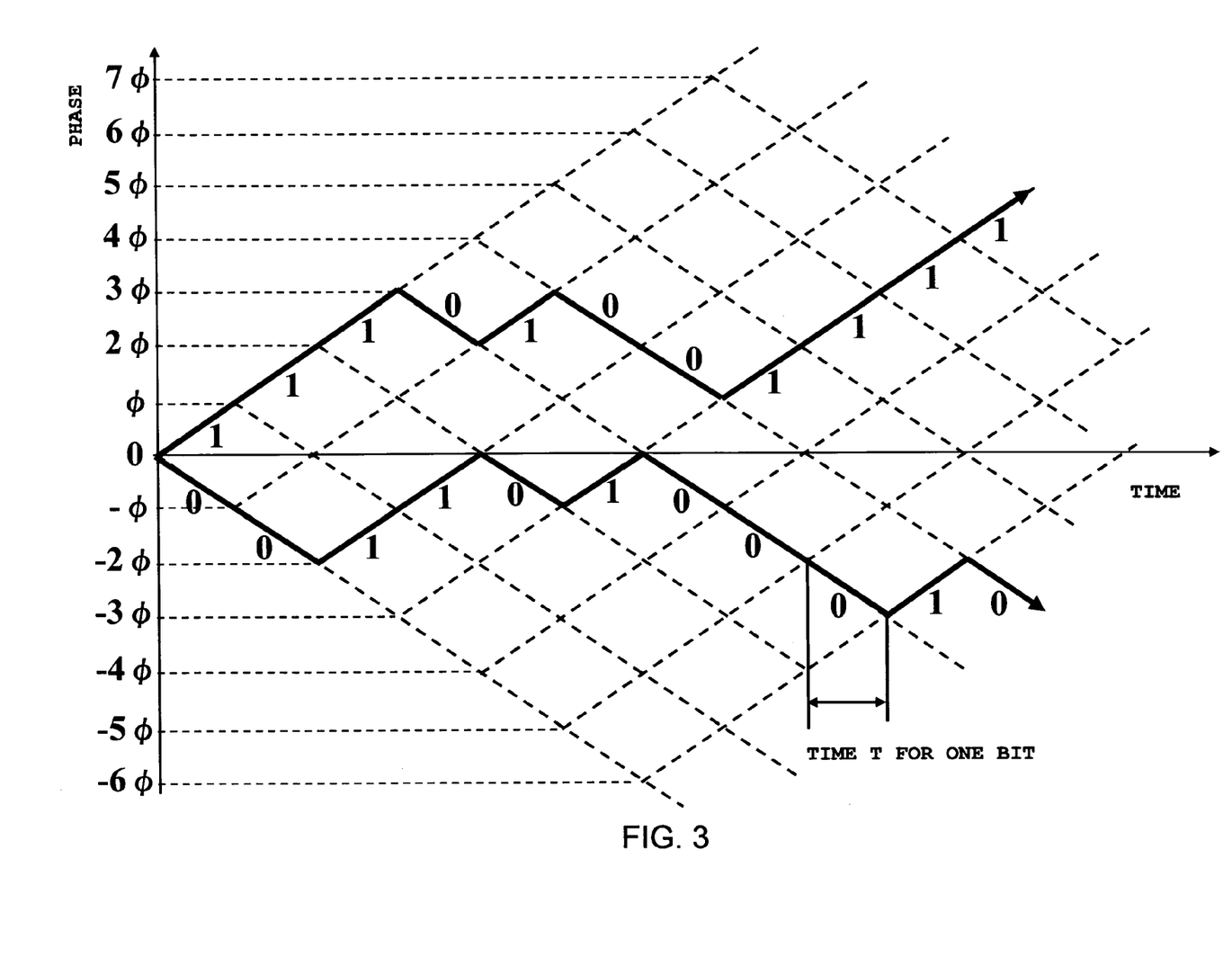
FIG. 3 is a view for explaining a phase variation of a continuous wave output from an FSK modulator.

FIG. 3 is a view for explaining a change in the phase of a continuous wave to be output from the FSK modulator. In FIG. 3, the phase of a carrier wave is continuously represented by 0, which is a fixed value, and an amount of phase rotation corresponding to frequency $f_1$ or $f_2$ is represented. In order to demodulate an FSK modulated signal, the only requirement is to discriminate the frequency of the signal. In the case of the continuous wave shown in FIG. 2(II), the signal shown in FIG. 2(II) can be demodulated to obtain the binary code shown in FIG. 2(I) by discriminating the frequency $f_1$ and the frequency $f_2$. If simply discriminating the frequencies is sufficient, it is not especially necessary to determine the phase of each frequency corresponding to a sign. For example, discontinuous change of the phase at the time of transition of sign would not cause any problems if simply discrimination of the frequencies is required. However, discontinuous phase at the time of transition of sign would accordingly result in an expansion of the frequency band. Therefore, by determining each frequency and the time length T for 1 bit such that the phase changes continuously at the time of transition of the sign, FSK modulation and demodulation can be performed in a narrower band width.

FIG. 3 illustrates a phase change of a continuous wave when the above conditions are satisfied. In the phase change of a continuous wave illustrated in FIG. 3, the phase changes continuously when a sign of the binary code changes; the phase of a continuous wave changes by +φ (i.e. advances by p) during a bit period in which the binary code is "1" (during the period of frequency $f_1$), and the phase of a continuous wave changes by −φ (i.e. delays by φ) during a bit period in which the binary code is "0" (during the period of frequency $f_2$).

The example continuous wave (FSK modulated wave) illustrated in FIG. 3 exhibits a feature that regardless of how the sign changes, the phase of the continuous wave changes continuously such that the phase always shifts on the ascending dotted line or the descending dotted line within the graph of FIG. 3. Further, by setting the frequency spacing corresponding to a sign to a somewhat small value, an FSK continuous wave in a narrow band can be obtained. The narrower the frequency spacing, the smaller the rotation of the phase in 1 bit. By setting the frequency spacing such that this phase rotation amount is π/2; i.e., by changing the phase of a continuous wave by +π/2 or −π/2 within 1 bit period, it is possible to perform transmission and reception of a digital signal with a digital error bit remaining reduced while maintaining the narrow band width. The FSK method in this case is especially referred to as an MSK (Minimum Shift Keying) method.

Figure 4:
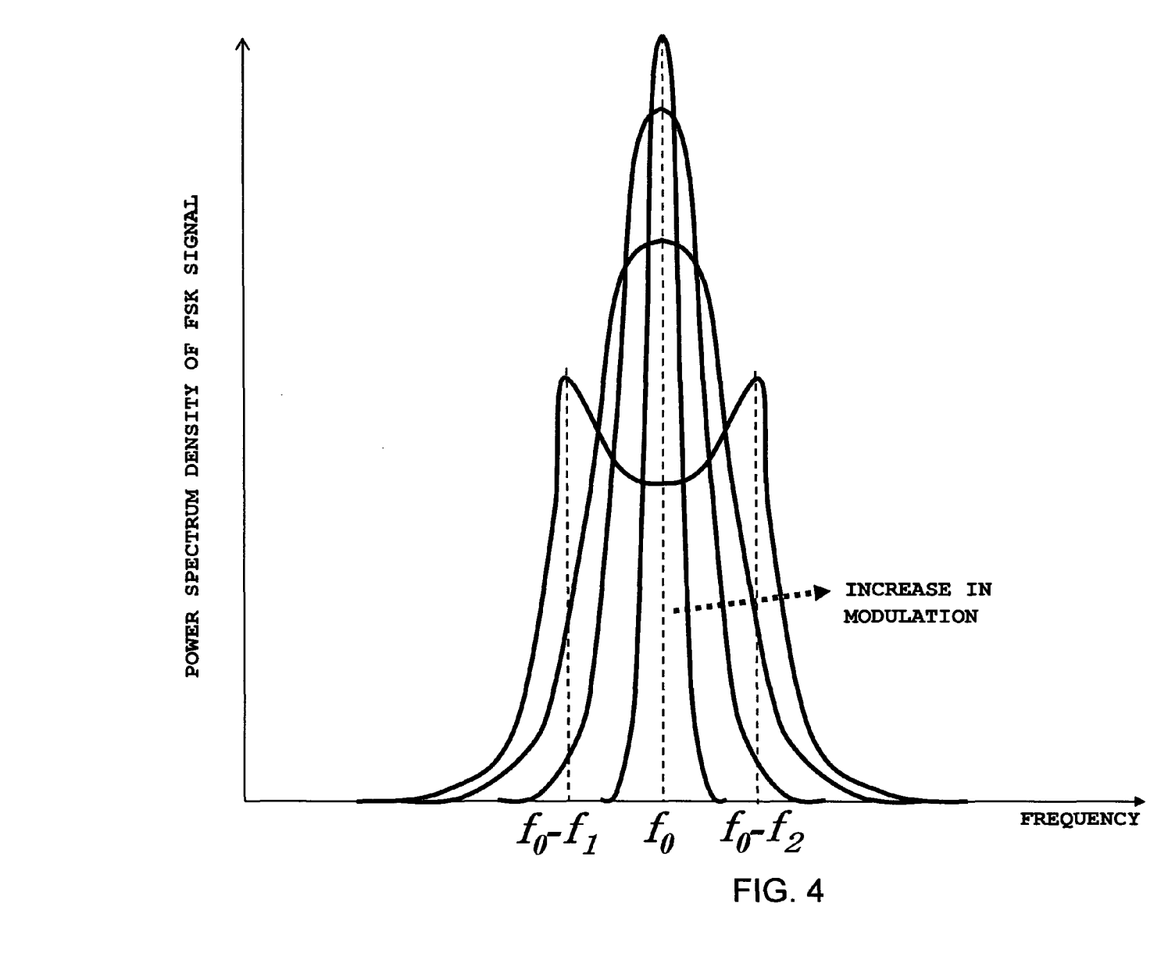
FIG. 4 is a view for explaining a frequency spectrum of a continuous wave output from the FSK modulator.

FIG. 4 is a view for explaining the frequency spectrum of a continuous wave to be output from the FSK modulator. In FIG. 4, the horizontal axis represents frequency and the vertical axis represents an electric power of each frequency component, and the graph illustrated in FIG. 4 shows a change in the frequency spectrum of an FSK signal (FSK continuous wave) having a frequency shifted by $f_1$ or $f_2$ with respect to a carrier wave (RF wave) having a frequency $f_0$ by means of frequency shift keying, in accordance with the degree of modulation. Here, the degree of modulation m of FSK is defined as follows:

$$m = |f_1 - f_2|T = \frac{|f_1 - f_2|}{f_b}, f_b = \frac{1}{T}$$

The degree of modulation m represented by the above formula is a ratio between the frequency difference (a difference between $f_1$ and $f_2$) and a bit rate $f_b$ (bit/s.), and has a meaning similar to the degree of modulation β of analog FM modulation. Increasing the degree of modulation m corresponds to setting a large frequency difference, resulting in spread of the frequency spectrum. It is therefore desirable to set the degree of modulation m in consideration of the frequency band of an ultrasound probe and so on, for example.

According to the present embodiment, delay processing is applied to the transmission signal which is formed by the FSK modulator (designated by reference numeral 20 in FIG. 1) to form a reference signal, and the reference signal is then used in the receiving mixer (designated by reference numeral 30 in FIG. 1) to perform mixer processing with respect to a reception signal (i.e., multiplication of the reference signal and the reception signal). In this mixer processing, the correlation between the reception signal from a depth corresponding to the phase of the reference signal having been subjected to delay processing (i.e., a depth of the target position) and the reference signal is increased to the maximum, whereas the correction between the reception signal from depths other than the depth of the target position and the reference signal is drastically reduced. As such, the ultrasound diagnosis apparatus according to the present embodiment has a function of position selectivity.

Figure 5:
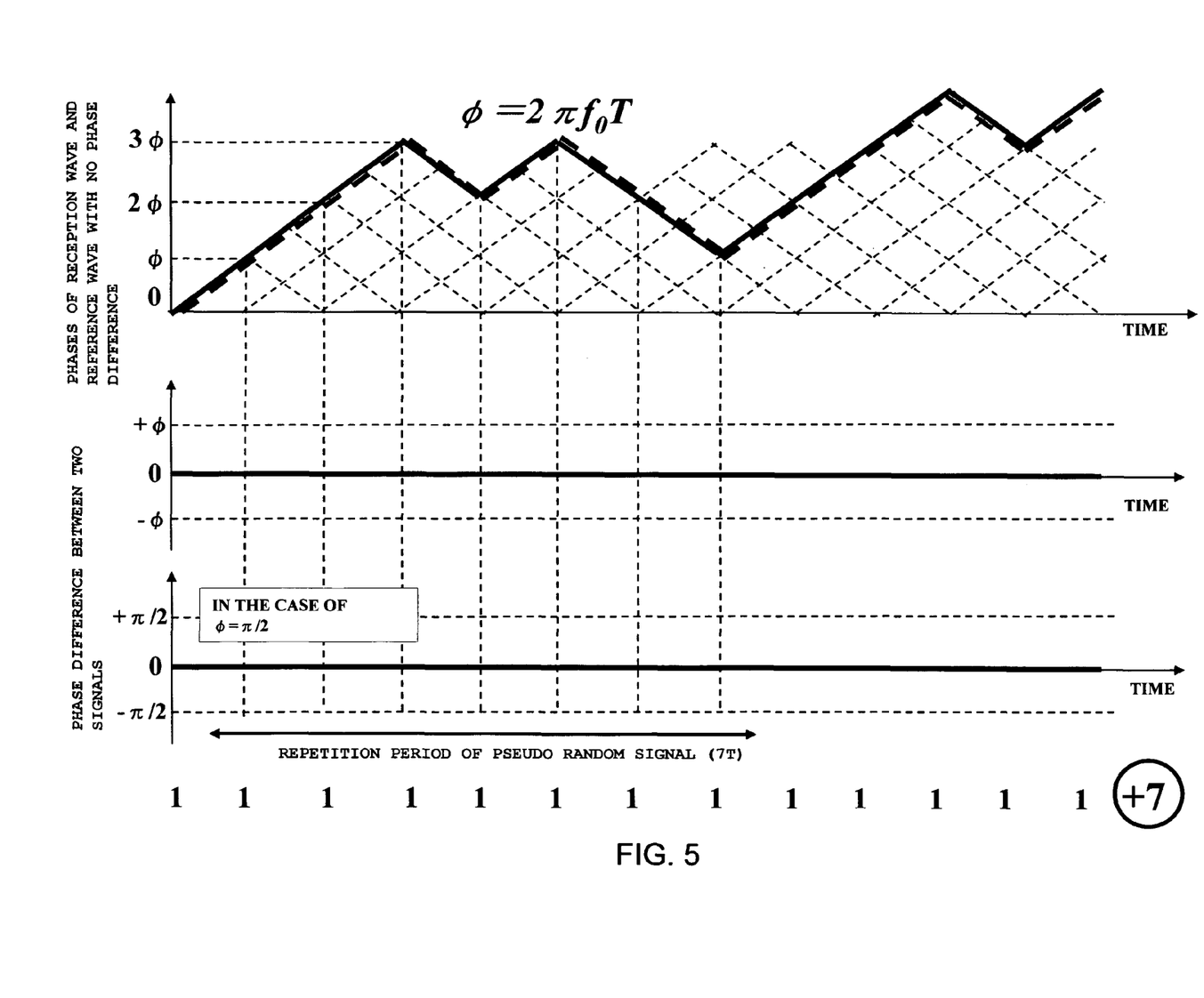
FIG. 5 is a view showing a state in which a phase of a reference signal matches a phase of a reception signal.
Figure 6:
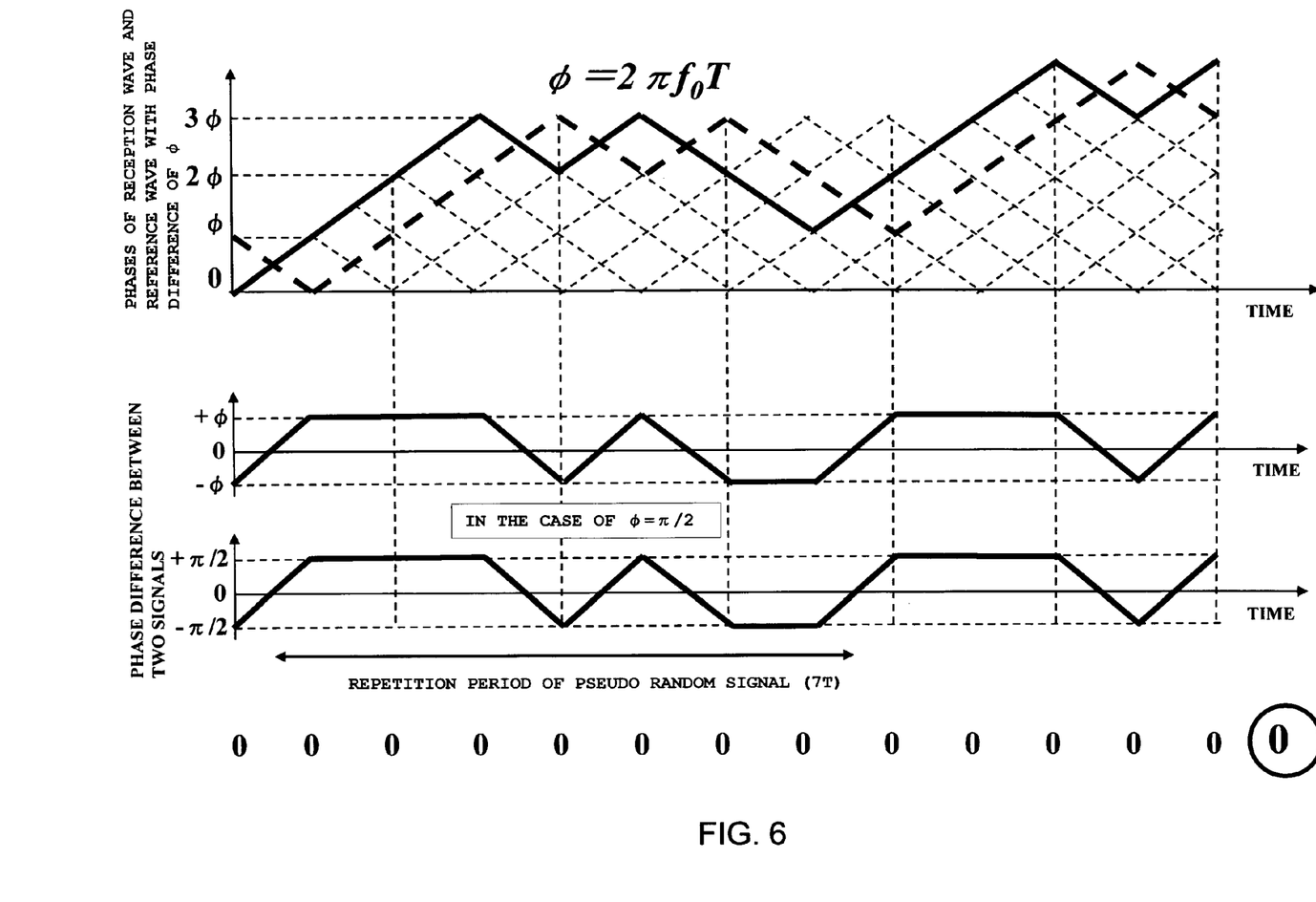
FIG. 6 is a view showing a state in which a phase of a reference signal is delayed by T.
Figure 7:
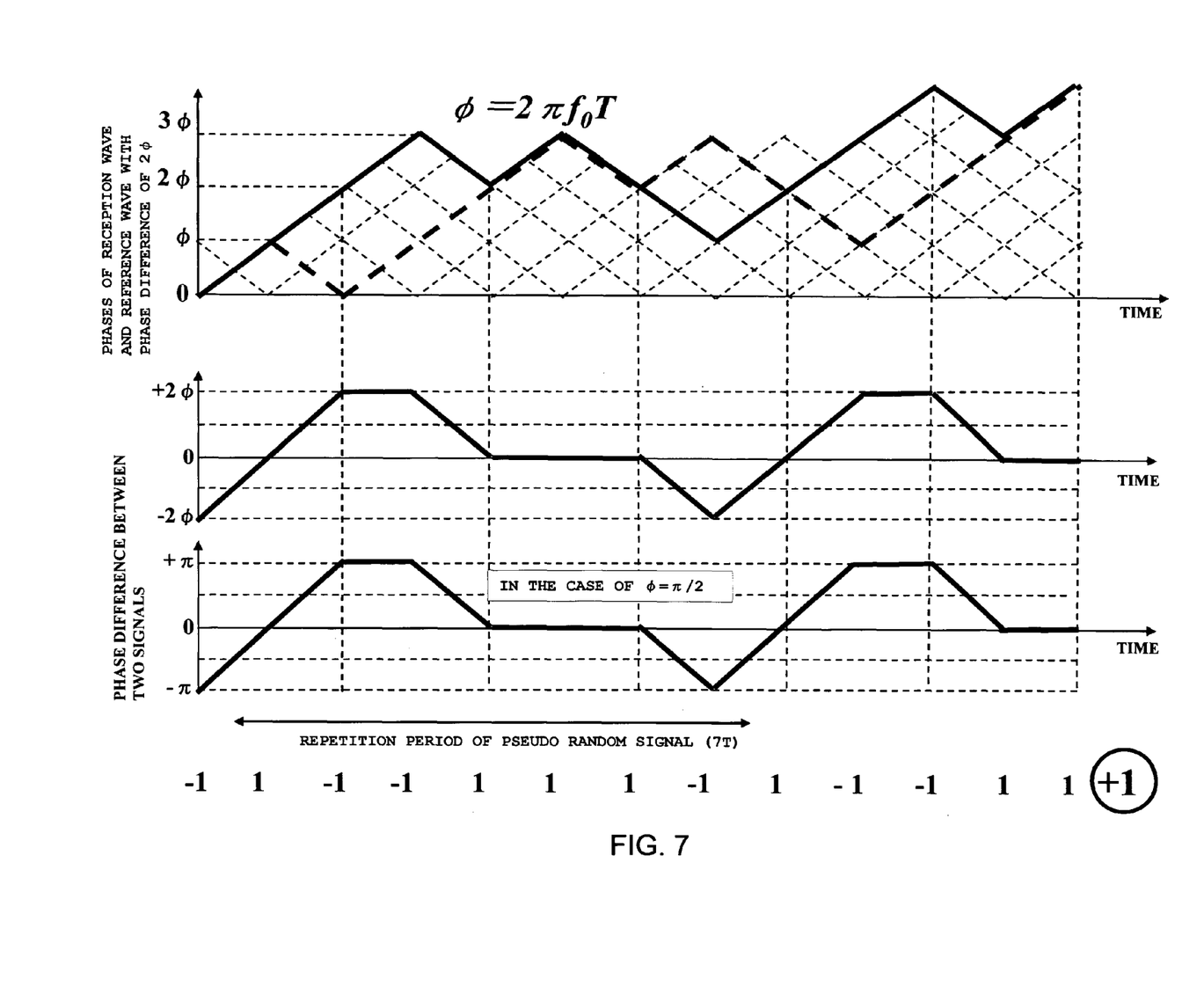
FIG. 7 is a view showing a state in which a phase of a reference signal is delayed by 2T.

FIGS. 5 to 7 are views for explaining position selectivity according to the present embodiment, each illustrating a temporal change in the phase of each of a reception signal (reception wave) from a target position and a reference signal (reference wave) and a temporal change in the phase difference between a reception signal from a target position and a reference signal. In each of FIGS. 5 to 7, a phase φ is a change in the phase of a continuous wave during 1 bit period T of a pseudo random signal. Further, each figure also illustrates a temporal change in the phase difference in the case of φ=π/2.

The multiplier (i.e., the receiving mixer 30 in FIG. 1) outputs a result (e.g., a voltage) in accordance with a phase difference between the reception signal and the reference signal. For example, the output value of the multiplier is "0" when the phase difference between these signals is π/2, 3π/2, −π/2, or −3π/2, the output value of the multiplier is "+1" when the phase difference between these signals is 0 or 2π, and the output value of the multiplier is "−1" when the phase difference between these signals is π or −π.

Here, while a pseudo random pattern which changes in a 7-bit period is used in the example shown in FIGS. 5 to 7, it is desirable to employ a pseudo random pattern which changes in a period of 100 to 200 bits, for example, at the time of implementation of the apparatus.

FIG. 5 illustrates a case in which the phase of the reference signal corresponds to the phase of a reception signal from the target position. When the phase of the reference signal corresponds to the phase of a reception signal from the target position, the phase difference between these signals is always 0. Assuming that the output from the multiplier (i.e., the receiving mixer 30 in FIG. 1) when the phase difference between the reference signal and the reception signal is 0 is "+1," a sum value of the multiplier outputs which can be obtained during a 7-bit period when the phases of these signals are identical with each other would be "+7."

Meanwhile, FIGS. 6 and 7 illustrate cases in which the phase of the reference signal does not correspond to that of a reception signal from the target position.

Specifically, FIG. 6 illustrates a case in which the phase of the reference signal (bold dotted line) is delayed with respect to that of the reception signal from a target position (solid line) by T. The phase difference between these signals in this case is as shown in the lower section of FIG. 6, in which the output from the multiplier (i.e., the receiving mixer 30 of FIG. 1) is always "0" in the case of $\phi=\pi/2$, and the sum value of the multiplier outputs which can be obtained during a 7-bit period is also "0."

FIG. 7 illustrates a case in which the phase of the reference signal (bold dotted line) is delayed with respect to that of the reception signal from a target position (solid line) by 2T. The phase difference between these signals in this case is as shown in the lower section of FIG. 7, in which, in the case of $\phi=\pi/2$, the output from the multiplier (i.e., the receiving mixer 30 of FIG. 1) is "+1" or "−1," which is repeated at random, and the sum value of the multiplier outputs which can be obtained during a 7-bit period is "+1."

As described above, the sum value of the multiplier outputs is "+7," which is extremely large, when the phase of a reference signal corresponds to the phase of a reception signal from a target position, whereas the sum value of the multiplier outputs is "0" or "+1," which is drastically smaller, when the phases of a reference signal and a reception signal do not correspond to each other.

Figure 8:
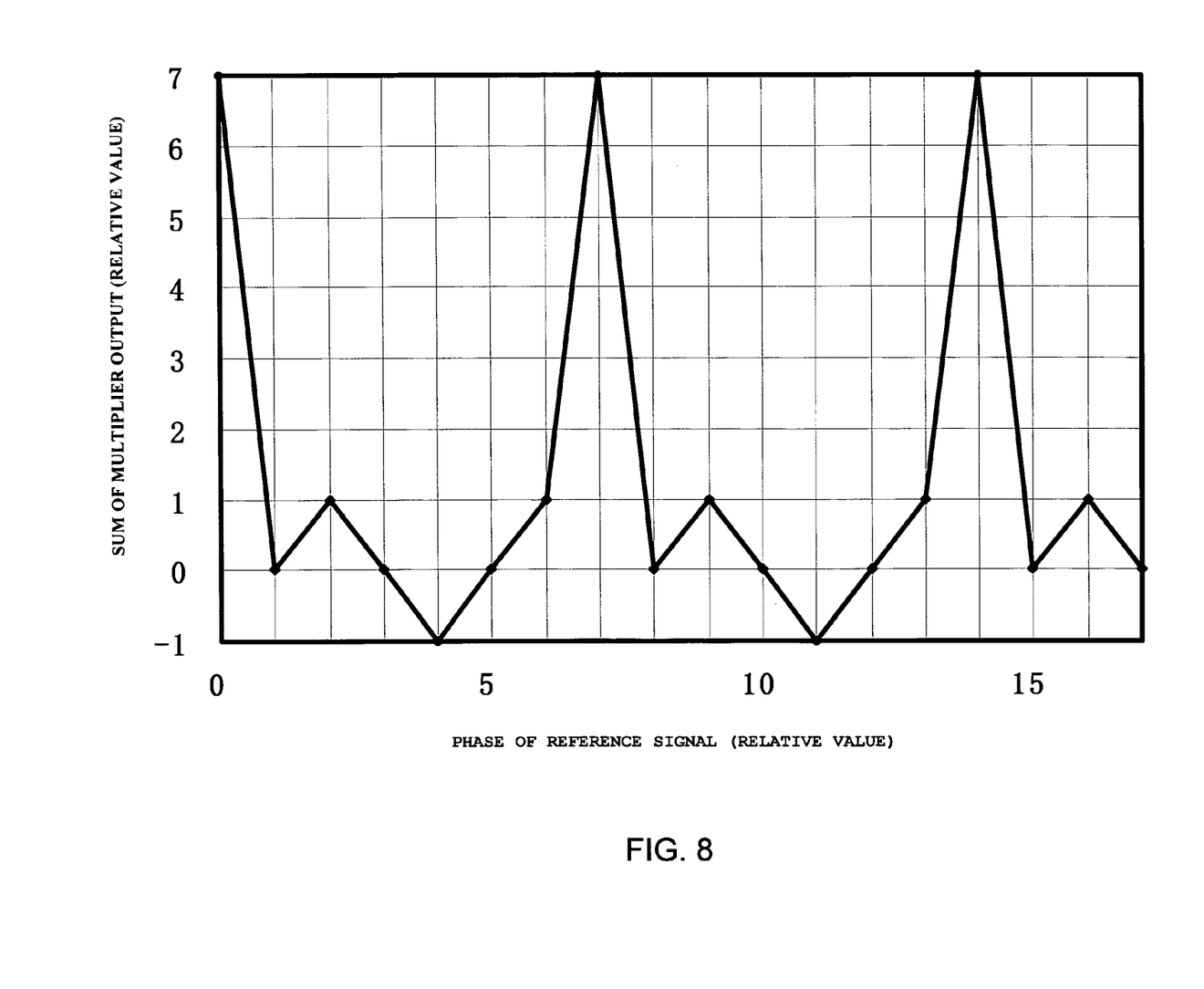
FIG. 8 is a diagram illustrating a relationship between the phase of a reference wave and a multiplier output.

FIG. 8 is a view illustrating a relationship between the phase of a reference signal and the multiplier output. The graph shown in FIG. 8 corresponds to the examples shown in FIGS. 5 to 7. In FIG. 8, the vertical axis of the graph represents a sum value of the multiplier outputs which can be obtained within a 7-bit period, and the horizontal axis represents the phase of a reference signal(reference wave) with respect to a reception signal; i.e., the phase difference between a reception signal and a reference signal. Here, the horizontal axis of FIG. 8 indicates a relative magnitude of the phase when $\phi=\pi/2$ is used as a reference (i.e., when $\phi=\pi/2$ is assumed to be "1").

When the phase difference between the reference signal and the reception signal is 0, the sum value of the multiplier outputs is "+7" as described above with reference to FIG. 5. Accordingly, in FIG. 8, the multiplier output value obtained when the phase of the reference wave is 0 is "+7." Further, as described above with reference to FIGS. 6 and 7, the sum value of the multiplier outputs is "0" when the phase difference is $\phi$, and the sum value of the multiplier outputs is "+1" when the phase difference is 2$\phi$. Accordingly, in FIG. 8, the multiplier output value obtained when the phase of the reference wave is 1 is "0," and the multiplier output value obtained when the phase of the reference wave is 2 is "+1."

FIG. 8 also illustrates multiplier output values obtained by further changing the phase of the reference signal to 3, 4, 5, 6, 7, and so on. As can be seen from the figure, the multiplier output value (a sum value within a 7-bit period) is a remarkably greater value, "+7," when the phase difference is 0, as compared with cases where the phase difference exists. Further, when the phase of the reference wave is shifted by 7 in relative value, because a pseudo random signal having a 7-bit period is shifted by an amount corresponding to one period, the multiplier output in this case also indicates a remarkably great value, "+7," similar to the case where the phase difference is 0.

As can be known from the above, according to the present embodiment, by adjusting the phase of the reference signal so as to correspond to the delay time to the target, it is possible to selectively detect a reflection wave power and Doppler information concerning only the target depth. Also, such selectivity becomes sharper as the length of the pseudo random pattern increases. Further, as the pattern length increases this selectivity approaches characteristics similar to the range gate of the pulse wave Doppler (PW Doppler). In other words, it is possible to obtain the merits of the pulse waves, while retaining the advantages of the continuous waves.

Figure 9:
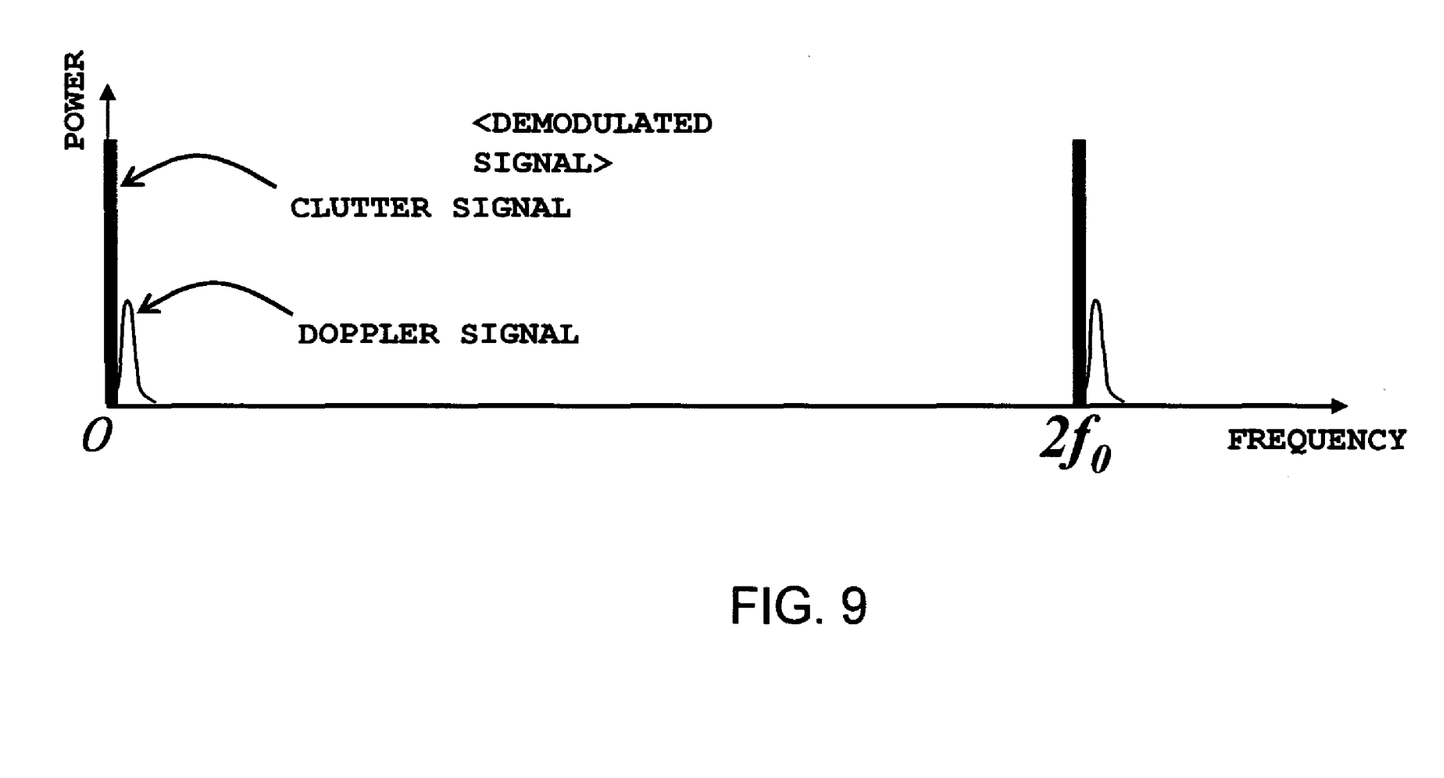
FIG. 9 is a view illustrating the frequency spectrum of a demodulated signal obtained by mixer processing.

FIG. 9 is a view for explaining a demodulated signal according to the present embodiment and illustrates the frequency spectrum of a demodulated signal obtained by mixer processing. The demodulated signal shown in FIG. 9 corresponds to a result of multiplication of a reference signal and a reception signal when the correlation thereof is maximized. In other words, the demodulated signal of FIG. 9 indicates a result of multiplication between a reception signal from a target position and a reference signal whose phase is matched to a depth of a target position.

The demodulated signal illustrated in FIG. 9 contains a direct current(low frequency) signal component, and a harmonic component which has twice the frequency $f_0$ of an RF signal. Here, as illustrated in FIG. 2(II), the frequency of the continuous wave which has been FSK modulated is random repetition of the frequency $f_1$ and the frequency $f_2$, for example. When a difference between the frequency $f_1$ and the frequency $f_2$ is smaller than the frequency $f_0$, a Doppler frequency spectrum corresponding to the frequency $f_1$ and a Doppler frequency spectrum corresponding to the frequency $f_2$ are detected in an overlapping manner near DC, so that the frequency spectrum as shown in FIG. 9 is obtained.

The Doppler signal appears attached to the direct current signal component and the harmonic component which is twice the frequency $f_0$ of the RF signal. Here, because the LPFs (designated by reference numerals 36 and 38 in FIG. 1) remove the harmonic component so that only the direct current(low frequency) signal components are extracted. Only the frequency spectrum of the direct current signal component illustrated in FIG. 9, is sent to the FFT circuits (designated by reference numerals 40 and 42 in FIG. 1). Then, in the Doppler information analyzing unit (designated by reference numeral 44 in FIG. 1), a Doppler signal is extracted from the frequency spectrum of the direct current signal component illustrated in FIG. 9, and the flow rate of blood existing at the target position, for example, is calculated based on the Doppler shift amount and so on. As orthogonal detection is performed in the receiving mixer (designated by reference numeral 30 in FIG. 1), it is also possible to determine the polarity of flow rate. Also, the position of a blood vessel wall, for example, existing at the target position may be obtained by extracting a clutter signal from the frequency spectrum of the direct current signal component.

Here, the attenuation characteristics at the time of propagation of ultrasound within the living organism is called frequency dependent attenuation (FDA), and is known to be substantially in proportion to the frequency and the propagation distance in a soft tissue within the living organism. The FDA affects the shape of the frequency spectrum of the demodulated signal. More specifically, when compared to the frequency spectrum of a demodulated signal obtained from near the body surface, the frequency spectrum of a demodulated signal obtained from a deeper position suffers from greater attenuation. Accordingly, compensation processing for the frequency dependent attenuation within the living organism may be applied to the frequency spectrum output from the FFT circuits (designated by reference numerals 40 and 42). For example, a signal obtained from a deeper position is amplified to a greater degree, thereby cancelling a variation in the attenuation amount in accordance with the position (depth). It is also possible to apply compensation processing for the frequency dependent attenuation to the output from the receiving mixer (designated by reference numeral 30 in FIG. 1).

Figure 10:
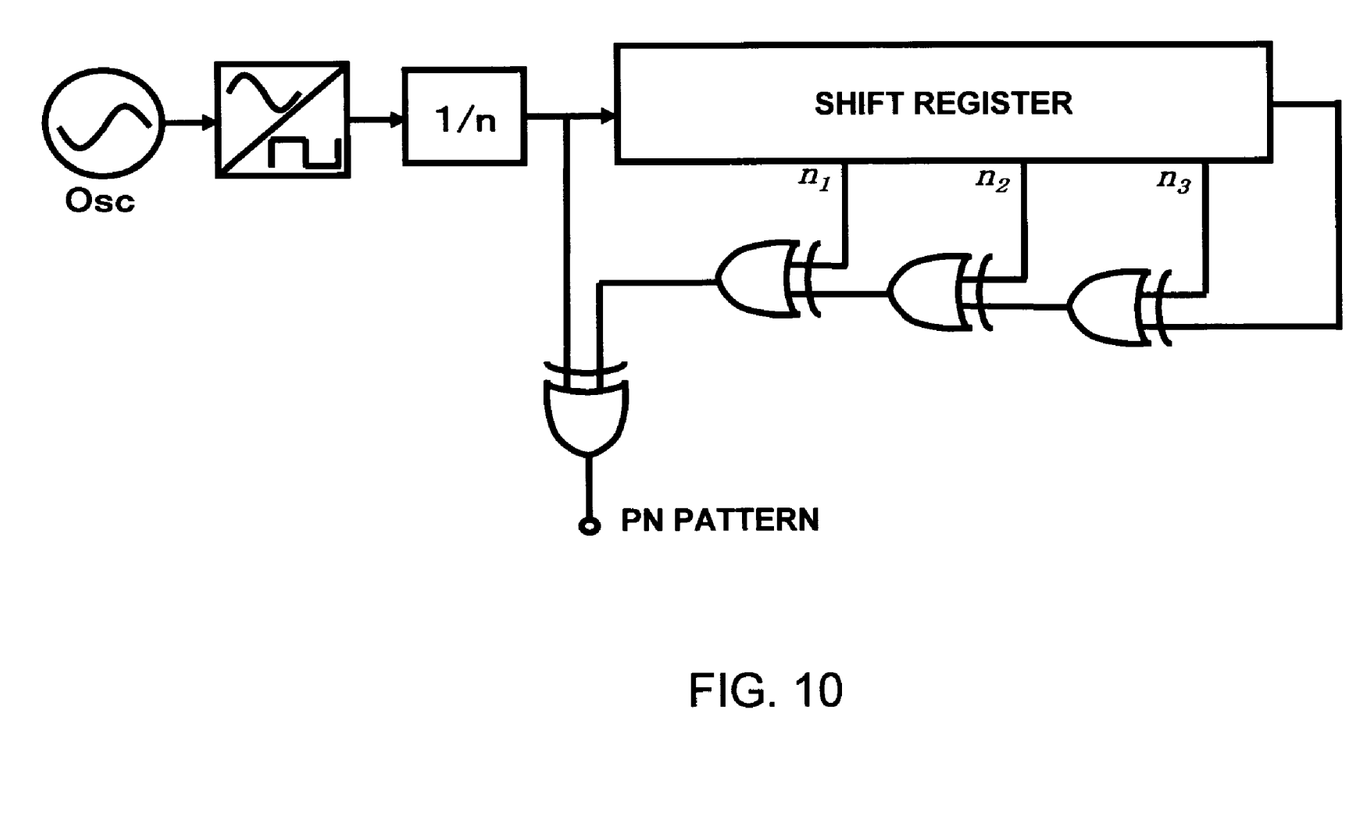
FIG. 10 is a view illustrating a specific example of a pattern generator.

FIG. 10 illustrates a specific example of the pattern generator (designated by reference numeral 24 in FIG. 1). In the example circuit structure illustrated in FIG. 10, a carrier wave (RF signal) output from a crystal oscillator (OSC) is transformed into a rectangular signal and is then n-frequency divided, and the resulting signal is input to the shift register. Further, outputs of $n_1$ to $n_3$ extracted from the intermediate stages of the shift register and an output from the last stage of the shift register are utilized to obtain an exclusive OR, so that a PN pattern can be obtained. When the shift register has n stages, the length of a PN pattern is $(2^n-1)$ bits. For example, when n=10, a PN pattern of 1023 bits can be configured in a simple manner. In this case, while the multiplier output obtained when the phases of the reception signal and the reference signal are completely identical with each other is 1023 times that for 1 bit, the outputs at other portions are at most several times that for 1 bit. It is therefore possible to significantly increase the selection ability. The circuit in FIG. 10, which can be configured by a digital circuit, is also advantageous in that IC can be achieved easily.

Based on a periodical signal sequence output from the pattern generator, the FSK modulator (designated by reference numeral 20 in FIG. 1) forms a continuous wave by applying frequency shift keying (FSK). The FSK modulator may employ a carrier wave with a frequency $f_1$ and a carrier wave with a frequency $f_2$ which are previously prepared, and appropriately select the carrier wave with the frequency $f_1$ or the carrier wave with the frequency $f_2$ in accordance with the PN pattern obtained by the circuit shown in FIG. 10, for example, such that the selected carrier waves are connected with each other on the time axis, thereby forming an FSK continuous wave.

Figure 11:
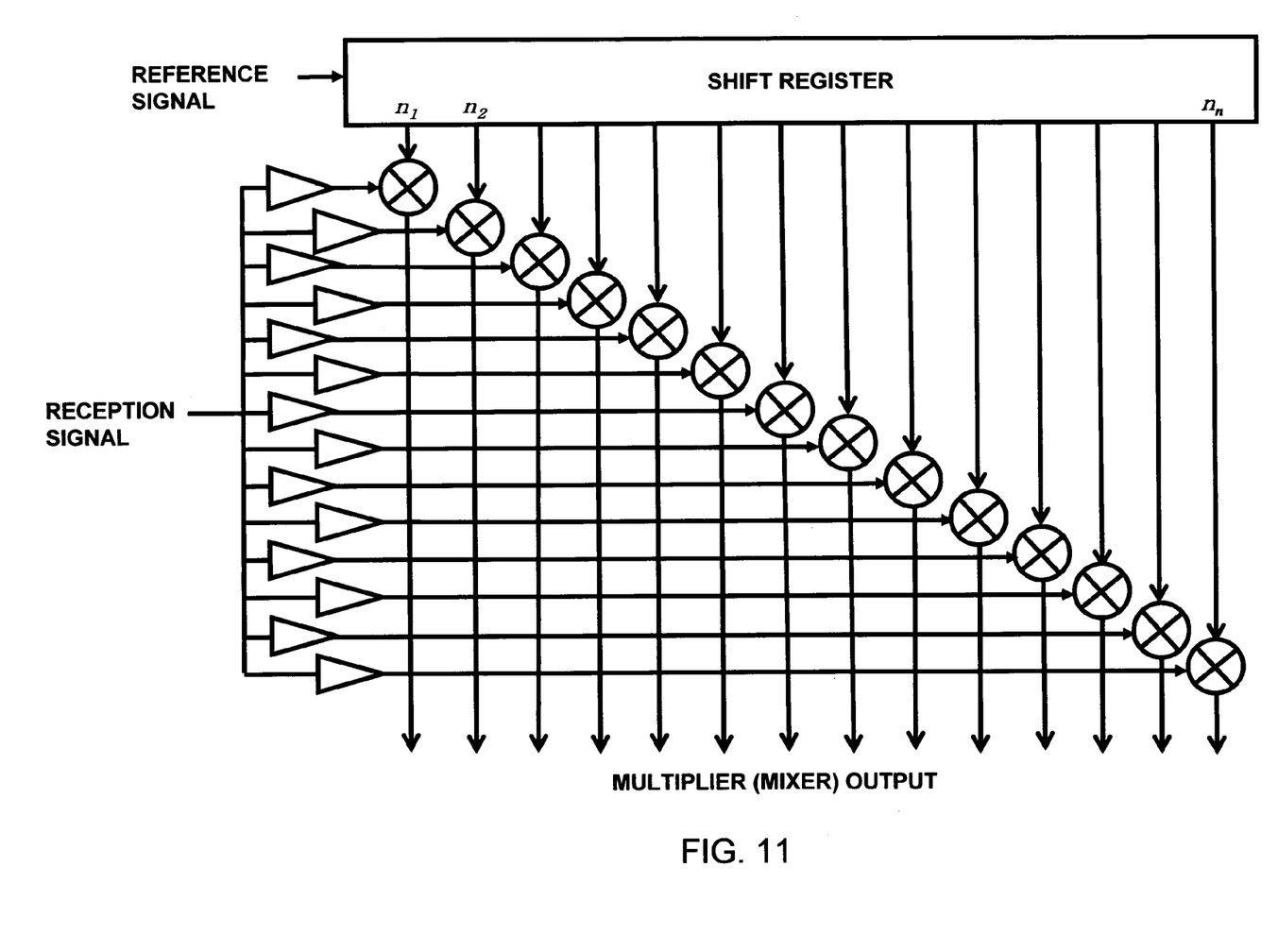
FIG. 11 is a view for explaining modification examples of a delay circuit and a receiving mixer.

FIG. 11 is a view for explaining a modification example of the delay circuit (designated by reference numerals 26I and 26Q in FIG. 1) and the receiving mixer (designated by reference numeral 30 in FIG. 1). In the circuit illustrated in FIG. 11, the reference signal is delayed by a n-stage shift register, and a plurality of delayed reference signals with different delay times with respect to each other are simultaneously output from the respective taps $n_1$ to $n_n$ of the shift register. Then, in each of n mixers corresponding to the respective taps $n_1$ to $n_n$ of the shift register, multiplication between the reception signal and each delayed reference signal is performed, so that a plurality of multiplication results corresponding to the plurality of delayed reference signals are output simultaneously (in parallel). By previously associating a plurality of target positions arranged in the depth direction within a living organism with the respective taps $n_1$ to $n_n$ of the shift register, Doppler information from a plurality of target positions can be acquired simultaneously. For example, it is possible to employ a configuration such that tissue information from all the positions along the ultrasound beam can be detected simultaneously.

While a preferred embodiment of the present invention and some modification examples have been described, they are merely illustrative examples in various respects, and do not therefore limit the scope of the present invention.

For example, although, in the embodiment described above, frequency shift keying (FSK) is utilized for digitally modulating a continuous wave, as is obvious to those with ordinary skill in the art, phase shift keying (PSK), amplitude shift keying (ASK), or the like may be utilized in place of FSK as a digital modulation method. Here, it is also possible to store data of a digitally modulated continuous wave in a memory and so on and generate the continuous wave based on the data read from the memory.

What is claimed is:

1. An ultrasound diagnostic apparatus comprising:
   a transmission signal processing unit that digitally modulates an input wave based on a periodical signal sequence to produce a digitally modulated continuous wave and outputs the digitally modulated continuous wave as a transmission signal;
   a transmitting/receiving unit that transmits a transmission wave corresponding to the transmission signal to a living organism and receives a reception wave associated with the transmission wave from the living organism, to thereby obtain a reception signal;
   a reception signal processing unit that applies demodulation processing to the reception signal by using a reference signal formed based on the transmission signal, to thereby obtain a demodulated signal; and
   an in-vivo information extraction unit that extracts in-vivo information from the demodulated signal,
   wherein in-vivo information from a target position within the living organism is selectively extracted.

2. The ultrasound diagnostic apparatus according to claim 1, wherein
   the transmission signal processing unit digitally modulates the input wave using frequency shift keying.

3. The ultrasound diagnostic apparatus according to claim 2, wherein
   the transmission signal processing unit digitally modulates the input wave by varying a frequency by means of frequency shift keying based on the periodical signal sequence.

4. The ultrasound diagnostic apparatus according to claim 3, wherein
   the transmission signal processing unit digitally modulates the input wave by varying a frequency while continuously changing a phase.

5. The ultrasound diagnostic apparatus according to claim 4, wherein
   the transmission signal processing unit digitally modulates the input wave by varying a phase by $+\pi/2$ or $-\pi/2$ for each signal of the periodical signal sequence, within a period T of each signal.

6. The ultrasound diagnostic apparatus according to claim 1, wherein
   the reception signal processing unit applies demodulation processing to the reception signal by using the reference signal having a waveform which is identical with that of the transmission signal.

7. The ultrasound diagnostic apparatus according to claim 1, wherein
the reception signal processing unit applies the demodulation processing to the reception signal by adjusting a correlation between a periodical signal sequence of a reception signal obtained from the target position within the living organism and a periodical signal sequence of the reference signal.

8. The ultrasound diagnostic apparatus according to claim 7, wherein
the correlation is adjusted by applying delay processing in accordance with a depth of the target position within the living organism to adjust a delay relationship between the reception signal and the reference signal.

9. The ultrasound diagnostic apparatus according to claim 8, wherein
with the delay processing, a correlation between the periodical signal sequence of the reception signal and the periodical signal sequence of the reference signal is enhanced.

10. The ultrasound diagnostic apparatus according to claim 9, wherein
by delaying the reference signal by a delay amount in accordance with a depth of the target position, a signal sequence pattern of the reception signal obtained from the target position and a signal sequence pattern of the reference signal are matched to each other.

11. The ultrasound diagnostic apparatus according to claim 1, wherein
the transmission signal processing unit digitally modulates the input wave by varying a frequency by means of frequency shift keying based on the periodical signal sequence, and the reception signal processing unit applies demodulation processing to the reception signal by using the reference signal having a waveform which is identical with that of the transmission signal.

12. The ultrasound diagnostic apparatus according to claim 11, wherein
Doppler information from the target position is selectively extracted by applying the demodulation processing with a correlation between a periodical signal sequence of a reception signal obtained from the target position within the living organism and a periodical signal sequence of the reference signal being adjusted.

13. The ultrasound diagnostic apparatus according to claim 12, wherein
by delaying the reference signal by a delay amount in accordance with a depth of the target position, a signal sequence pattern of the reception signal obtained from the target position and a signal sequence pattern of the reference signal are matched to each other.

14. The ultrasound diagnostic apparatus according to claim 1, wherein
the in-vivo information extraction unit extracts, as in-vivo information, a Doppler signal component corresponding to a direct current signal component contained in the demodulated signal.

15. The ultrasound diagnostic apparatus according to claim 1, further comprising:
a delay processing unit that delays the reference signal based on a plurality of different delay amounts, to thereby form a plurality of delayed reference signals corresponding to a plurality of target positions,
wherein the reception signal processing unit applies demodulation processing to the reception signal by using the plurality of delayed reference signals, to thereby form a plurality of demodulated signals corresponding to the plurality of target positions, and the in-vivo information extraction unit extracts, based on the plurality of demodulated signals, in-vivo information from the plurality of target positions arranged in a depth direction within the living organism.

16. An ultrasound diagnostic apparatus comprising:
a memory which stores data of a continuous wave having been digitally modulated based on a periodical signal sequence;
a transmission signal processing unit that forms a transmission signal of the continuous wave based on the data stored in the memory and outputs the transmission signal;
a transmitting/receiving unit that transmits a transmission wave corresponding to the transmission signal to a living organism and receives a reception wave associated with the transmission wave from the living organism, to thereby obtain a reception signal;
a reception signal processing unit that applies demodulation processing to the reception signal by using a reference signal formed based on the transmission signal, to thereby obtain a demodulated signal; and
an in-vivo information extraction unit that extracts in-vivo information from the demodulated signal,
wherein in-vivo information from a target position within the living organism is selectively extracted.

* * * * *